United States Patent
Ochsner et al.

(10) Patent No.: US 9,669,147 B2
(45) Date of Patent: Jun. 6, 2017

(54) BIOMEDICAL APPARATUS FOR PUMPING BLOOD OF A HUMAN OR AN ANIMAL PATIENT THROUGH A SECONDARY INTRA- OR EXTRACORPOREAL BLOOD CIRCUIT

(71) Applicant: ETH Zurich, Zurich (CH)

(72) Inventors: Gregor Ochsner, Einsiedeln (CH); Lino Guzzella, Uster (CH); Marianne Schmid Daners, Schaffhausen (CH); Raffael Amacher, Pfaffikon (CH)

(73) Assignee: ETH Zurich, Zurich (CH)

( * ) Notice: Subject to any disclaimer, the term of this patent is extended or adjusted under 35 U.S.C. 154(b) by 0 days.

(21) Appl. No.: 14/786,242

(22) PCT Filed: Apr. 22, 2014

(86) PCT No.: PCT/EP2014/001064
§ 371 (c)(1),
(2) Date: Oct. 22, 2015

(87) PCT Pub. No.: WO2014/173527
PCT Pub. Date: Oct. 30, 2014

(65) Prior Publication Data
US 2016/0101230 A1    Apr. 14, 2016

(30) Foreign Application Priority Data
Apr. 24, 2013   (EP) ................... 13002157

(51) Int. Cl.
*A61M 1/12* (2006.01)
*A61M 1/36* (2006.01)
(Continued)

(52) U.S. Cl.
CPC ........... *A61M 1/3607* (2014.02); *A61B 5/029* (2013.01); *A61B 5/02028* (2013.01);
(Continued)

(58) Field of Classification Search
None
See application file for complete search history.

(56) References Cited

U.S. PATENT DOCUMENTS 4,925,443 A * 5/1990 Heilman ............. A61M 1/1068
600/16
6,298,269 B1 * 10/2001 Sweeney ............ A61N 1/36528
607/28

(Continued)

FOREIGN PATENT DOCUMENTS

EP    2298375 A1    3/2011
WO    0069490 A1    11/2000
(Continued)

OTHER PUBLICATIONS

Glower et al., "Linearity of the Frank-Starling relationship in the intact heart: the concept of preload recruitable stroke work", Circulation, 1985, p. 994-1009, vol. 71, No. 5.

(Continued)

*Primary Examiner* — Kennedy Schaetzle
(74) *Attorney, Agent, or Firm* — The Webb Law Firm (57) ABSTRACT

A biomedical apparatus for pumping blood of a human or an animal patient through a secondary blood circuit is provided, including a blood pump (10), an inlet duct (11) and an outlet duct (12) for guiding blood of the patient to the blood pump (10) and back to the patient. The device further includes a measuring device (14) for measuring a physical parameter of the heart (2) or of a blood vessel, and a controller (13) for regulating the power of the blood pump (10). The measuring device (14) is adapted to be arranged inside the heart (2) or the blood vessel, and the controller is configured to determine an estimate for an inner volume of the heart (2) or of the blood vessel based on the physical parameter and is configured to regulate the power of the blood pump (10) depending on this estimate.

14 Claims, 3 Drawing Sheets (51) Int. Cl.
*A61B 5/107* (2006.01)
*A61B 5/00* (2006.01)
*A61B 8/00* (2006.01)
*A61B 5/02* (2006.01)
*A61B 5/029* (2006.01)
*A61B 5/15* (2006.01)
*A61B 8/12* (2006.01)
*A61M 1/10* (2006.01)

(52) U.S. Cl.
CPC .......... *A61B 5/1073* (2013.01); *A61B 5/1076* (2013.01); *A61B 5/15003* (2013.01); *A61B 5/150229* (2013.01); *A61B 5/4836* (2013.01); *A61B 5/6869* (2013.01); *A61B 8/00* (2013.01); *A61B 8/12* (2013.01); *A61B 8/4245* (2013.01); *A61M 1/1086* (2013.01); *A61M 1/122* (2014.02); *A61M 1/3666* (2013.01); *A61B 5/150992* (2013.01); *A61B 5/6876* (2013.01); *A61M 1/101* (2013.01); *A61M 2205/04* (2013.01); *A61M 2205/3303* (2013.01); *A61M 2205/3375* (2013.01); *A61M 2205/353* (2013.01); *A61M 2205/3515* (2013.01); *A61M 2230/04* (2013.01)

(56) References Cited

U.S. PATENT DOCUMENTS

| | | | |
|---|---|---|---|
| 6,360,123 B1* | 3/2002 | Kimchi | A61B 5/0215 324/600 |
| 6,422,990 B1* | 7/2002 | Prem | A61M 1/101 600/17 |
| 6,438,408 B1* | 8/2002 | Mulligan | A61N 1/36564 600/510 |
| 6,918,870 B1 | 7/2005 | Hunyor et al. | |
| 2002/0173693 A1* | 11/2002 | Landesberg | A61M 1/1046 600/16 |
| 2003/0032853 A1 | 2/2003 | Korakianitis et al. | |
| 2007/0073393 A1 | 3/2007 | Kung et al. | |
| 2008/0097226 A1* | 4/2008 | McConnell | A61B 5/0215 600/485 |
| 2011/0270331 A1* | 11/2011 | Peters | A61M 1/1068 607/3 |
| 2014/0114202 A1* | 4/2014 | Hein | A61B 5/6848 600/486 |
| 2015/0246166 A1* | 9/2015 | Greatrex | A61M 1/101 600/17 |
| 2015/0306290 A1* | 10/2015 | Rosenberg | A61B 5/6869 600/17 |

FOREIGN PATENT DOCUMENTS

| | | |
|---|---|---|
| WO | 02065908 A1 | 8/2002 |
| WO | 2004073796 A2 | 9/2004 |
| WO | 2008104858 A2 | 9/2008 |
| WO | 2012167876 A1 | 12/2012 |

OTHER PUBLICATIONS

Guyton et al., "Cardiac Output, Venous Return, and Their Regulation", Textbook of Medical Physiology 12th Ed., 2011, Chapter 20, p. 229-241, Saunders Elsevier Inc.

Takeuchi et al., "Comparison between preload recruitable stroke work and the end-systolic pressure-volume relationship in man", European Heart Journal, 1992, p. 80-84, vol. 13.

* cited by examiner

BIOMEDICAL APPARATUS FOR PUMPING BLOOD OF A HUMAN OR AN ANIMAL PATIENT THROUGH A SECONDARY INTRA- OR EXTRACORPOREAL BLOOD CIRCUIT

CROSS-REFERENCE TO RELATED APPLICATIONS

This application is the United States national phase of International Application No. PCT/EP2014/001064 filed Apr. 22, 2014, and claims priority to European Patent Application No. 13002157.9 filed Apr. 24, 2013, the disclosures of which are hereby incorporated in their entirety by reference.

TECHNICAL FIELD

The present invention concerns a biomedical apparatus for pumping blood of a human or an animal patient through a secondary intra- or extracorporeal blood circuit. The invention also concerns a method for operating such a biomedical apparatus.

PRIOR ART

Various applications exist in which the blood of a human or an animal patient needs to be pumped through a secondary intra- or extracorporeal blood circuit. These applications include for example mechanical circulatory support by means of ventricular assist devices (VADs), the circulation of blood by means of a heart-lung machine, also referred to as cardiopulmonary bypass, or extracorporeal membrane oxygenation (ECMO). These applications have in common that blood from a patient is guided to a blood pump by means of an inlet duct, and from the blood pump through an outlet duct back to the patient's circulatory system.

Ventricular assist devices (VADs) are used, when sufficient blood perfusion of patients with severe heart failure is to be restored by means of a mechanical blood pump. Even though the most preferred and accepted way to treat patients with severe heart failure is transplantation, VADs are often used to partly or completely restore the blood perfusion of the patients for bridging the time period until transplantation. While VADs have originally been developed for bridging to transplantation, the shortage of donor hearts has shifted the focus of clinicians and VAD developers to destination therapy and bridge to recovery. Bridge to recovery aims at later explantation of the VAD, due to recovery of the cardiac function during mechanical circulatory support. Destination therapy denotes the use of a VAD as a permanent implant. While recovery is the most desirable outcome of VAD therapy, only few patients show enough improvement in their cardiac function permitting the removal of the VAD. Thus, destination therapy remains a valid option for the treatment of severe heart failure.

VADs can be categorized into three pump-type generations. First generation VADs are pneumatically or electrically actuated pulsatile volumetric pumps. Pulsatile VADs imitate the working principle of the human heart and require a pump chamber and two unidirectional-flow valves. These devices are bulky and inefficient but provide a physiological perfusion. Pulsatile VADs are nowadays used mainly for bi-ventricular support, where the balance between the left and the right ventricle poses an additional problem. Second generation VADs are axial or centrifugal turbodynamic pumps with classical contact bearings. These devices exert a pressure on the blood by a spinning rotor in the blood stream. Modern, third generation VADs are axial or centrifugal turbodynamic pumps with a magnetically levitated rotor or with a blood-immersed bearing. Second and third generation devices are small, efficient, and more reliable. Compared to pulsatile VADs, these devices, however, provide non-physiological perfusion.

A problem with VADs, and with biomedical apparatuses for pumping blood through a secondary intra- or extracorporeal blood circuit in general, concerns the controlling of the output power of the blood pump being used in these devices. Most clinically used turbodynamic VADs, for example, are operated at a constant speed and the perfusion of VAD patients therefore shows only a minor adaptation to the demand. The requirements for a physiological control of blood pumps, however, are manifold and potentially conflicting. Since a controller for a turbodynamic VAD, as an example, has only one degree of freedom—the pump speed—it is not possible to meet several requirements simultaneously. It is, however, possible to reduce the set of requirements to one task: The physiological controller must prevent overpumping or underpumping, and within these limits, adapt the pump speed to meet the patient's demand. Overpumping denotes a misactuation of the VAD where the pump speed is chosen too high, which can lead to a complete emptying of the ventricle and eventually to ventricular suction. Underpumping denotes the situation where the pump speed is chosen too low, which leads to backflow through the pump and a congestion of blood before the left ventricle. This congestion increases left atrial and pulmonary venous pressures and can eventually lead to lung edema. Stagnation or backflow in the pump additionally promotes hemolysis, which is to be avoided.

In the document WO 2004/073796, methods are described for regulating the blood flow rate or blood pressure in a secondary blood circuit, in order to achieve a desired blood flow rate or blood pressure in the (primary) circulatory system of a patient. For regulating the blood pump, it is suggested in this document to monitor the blood flow rate or the blood pressure in the heart or the blood vessel of the patient.

The documents WO 00/69490, WO 02/065908 and U.S. Pat. No. 6,422,990 disclose VADs in which the pump speed is controlled based on measurements of external dimensions of the heart by means of sonomicrometry. The disadvantage of these devices is that a plurality of sensors has to be attached to the heart, which requires additional medical interventions for the patient. As an additional drawback, sonomicrometry only allows to measure the distances between the sensors and, therefore, does not necessarily consider the real physical conditions of the heart.

SUMMARY OF THE INVENTION

It is an object of the present invention to provide a biomedical apparatus for pumping blood of a human or an animal patient through a secondary intra- or extracorporeal blood circuit, in which the blood pump can be regulated in a physiological way.

In order to achieve this object, the present invention provides a biomedical apparatus for pumping blood of a human or an animal patient through a secondary intra- or extracorporeal blood circuit, comprising a blood pump for pumping blood, an inlet duct connected to the blood pump, for being inserted into a patient's circulatory system, in order to guide blood of the patient to the blood pump, and an outlet duct connected to the blood pump, for being inserted into the patient's circulatory system, in order to guide blood from the blood pump back to the patient's circulatory system. The biomedical apparatus further comprises a measuring device for measuring at least one physical parameter of the heart or of a blood vessel of the patient, and a controller for regulating the power of the blood pump based on the measured at least one physical parameter. The measuring device is adapted to be arranged inside the heart or the blood vessel, and the controller is configured to determine an estimate for an inner volume of the heart or of the blood vessel based on the measured at least one physical parameter and is configured to regulate the power of the blood pump depending on this estimate.

The strategy to determine an estimate for an inner volume of the heart or of the blood vessel is inspired by the Frank-Starling law describing the physiological behaviour of the stroke volume of the heart depending on the volume of the heart. According to this law, the stroke volume increases in response to an increase in the volume of blood filling the heart (the end-diastolic volume) when all other factors remain constant. Thus, by determining an estimate for an inner volume of the heart or of the blood vessel and by using this estimate for regulating the power of the blood pump, a very physiological way of regulating the blood pump is provided, in which the controller adapts the pump speed according to the patient's perfusion demand. Hence, the controller is able to adapt the cardiac output very similarly to the physiological heart. The determination of an accurate and precise estimate for the inner volume becomes possible by arranging the measuring device inside the heart or the blood vessel, and in particular inside the inner volume to be measured. By using an estimate for an inner volume of the heart or of the blood vessel, in order to control the blood pump, over- and underpumping are usually effectively prevented without any further measures.

The biomedical apparatus is preferably a Ventricular Assist Device (VAD), a heart-lung machine or an extracorporeal membrane oxygenation (ECMO) apparatus. Further types of biomedical apparatuses are conceivable, such as for example a dialysis apparatus. Depending on the type of apparatus, the blood is pumped through a secondary intra- or extracorporeal blood circuit. The secondary blood circuit here refers to an additional, artificial circuit, in which blood from the (primary) circulatory system of the patient is guided to a blood pump, which pumps the blood back into the circulatory system of the patient. Within the secondary blood circuit, the blood can optionally be treated in a certain way. For example, the blood can be oxygenated (ECMO, cardiopulmonary bypass), or waste and excess water can be removed from the blood (dialysis). In these cases, in which a treatment of the blood is carried out, the secondary blood circuit is usually an extracorporeal blood circuit. In cases, in which the main function of the biomedical apparatus is to support or to replace at least a part of the function of the heart, such as in the case of a VAD, the secondary blood circuit is preferably, but not necessarily, an intracorporeal blood circuit, i.e. a blood circuit being entirely arranged within the body of the patient.

The inlet duct and the outlet duct usually have a tubular form. They can be represented for example by flexible tubes. Preferably, however, the inlet duct is an inlet cannula and/or the outlet duct is an outlet cannula. Especially if the biomedical apparatus is a VAD, the inlet duct is advantageously adapted for being inserted into the heart, more advantageously for being inserted into one of the ventricles, and most advantageously for being inserted into the left ventricle, of the patient. In the case of a VAD, the outlet duct is preferably adapted to be inserted into the aorta of the patient.

The biomedical apparatus usually comprises a housing in which the blood pump and preferably also the controller are located. The apparatus usually also comprises an energy storage device, such as a battery or accumulator, or an electrical power connector for connecting the apparatus to an electrical power supply, in order to supply the blood pump with energy. The energy storage device is advantageously included in the housing of the apparatus.

The blood pump is preferably a pneumatically or electrically actuated pump. Other types of pumps, such as hydraulically actuated pumps, are also conceivable of course. The blood pump can be a pulsatile volume displacement pump or a pump relying on a rotating impeller. The pump can particularly be an axial or a centrifugal turbodynamic pump with classical contact bearings, with a magnetically levitated rotor or with a blood-immersed bearing.

Due to the physiological regulation of the pump power based on the inner volume, it would even be possible to use a turbodynamic VAD for bi-ventricular support.

The controller is provided for regulating the power, in particular the output power, of the blood pump based on the measured at least one physical parameter. The output power of the blood pump, which is particularly dependent on the motor speed of the blood pump, directly influences the blood volume being pumped by the blood pump per time unit, i.e. the blood rate.

By means of the measuring device and the controller, an estimate for an inner volume of the heart or the blood vessel can be determined. Preferably, the controller is configured to determine an estimate for an inner volume of the heart or of the blood vessel at end-diastole, in order to regulate the blood pump in a physiological way according to the Frank-Starling law. In a patient with a non-asystolic cardiac function, the at least one physical parameter is preferably measured such, that it reflects the periodic time curve of the volumetric change associated to the cardiac cycles. The inner volume reflected by the estimate is preferably the inner volume of one of the atria or the ventricles of the heart, in particular of the left ventricle, or the inner volume of a blood vessel determined over a certain length along the longitudinal direction of the blood vessel.

In order to achieve a sufficient temporal resolution for obtaining information concerning the change of the inner volume over the cardiac cycle and for achieving an optimal physiological regulation of the blood pump, the measuring device is preferably suited to measure the physical parameter with a temporal resolution of less than 400 ms, more preferably of less than 200 ms, and most preferably of less than 100 ms. Accordingly, the biomedical apparatus is preferably configured to measure the physical parameter with a temporal resolution of less than 400 ms, more preferably of less than 200 ms, and most preferably of less than 100 ms.

Optionally, but not necessarily, the biomedical apparatus can comprise a suction detector, in order to prevent ventricular or vascular suction. The suction detector can be used as an add-on to the physiological regulation of the blood pump based on the measured physical parameter. As soon as suction occurs, the suction detector detects it and a suction release strategy is initiated, which temporarily overrules the physiological controller.

In a particularly preferred embodiment, the measuring device is arranged on the inlet duct, in particular in the region of a free end of the inlet duct. With such an embodiment, the implantation for example of a VAD in the body of the patient is particularly simple and associated with a minimal risk for the patient, because the implantation then usually does not comprise any additional steps as compared to the implantation of a customary VAD. Only the inlet duct and the outlet duct have to be inserted into the circulatory system of the patient, and no additional implantation or attachment of sensors or any further components to the heart or the blood vessel are necessary.

The physical parameter is advantageously a distance between the measuring device and a ventricular wall of the heart or a distance between the measuring device and a vascular wall of the blood vessel. Thus, the measuring device is advantageously adapted for measuring at least one distance between the measuring device and a ventricular wall or between the measuring device and a vascular wall. The measurement of such a distance allows an accurate determination of the estimate for an inner volume of the heart of the blood vessel.

In order to obtain a precise estimate for the inner volume, the measuring device is advantageously adapted for measuring a plurality of distances between the measuring device and the ventricular wall or between the measuring device and the vascular wall in differing directions. A precise estimate for the inner volume can then be obtained, especially if all of these measured distances are combined for the determination of the estimate. The distances are preferably simultaneously measured in differing directions.

In a particularly preferred embodiment, the measuring device is a device which allows sending out an electromagnetical or a mechanical wave and which advantageously also allows receiving reflections of this wave, the reflections usually occurring due to tissue boundaries in the heart or in the blood vessel. By determining the travel time of the reflected wave, distances between tissue boundaries and the measuring device can be calculated. Preferably, the wave is an ultrasound wave and the measuring device is an ultrasound measuring device suited for carrying out ultrasound measurements. In this case, the measuring device advantageously comprises a plurality of ultrasound transducers, in particular ultrasound transceivers. In order to achieve an adequate spatial resolution and a sufficiently strong (reflected) signal with regard to the measurement data, the ultrasound measuring device preferably operates in a frequency range from 20 kHz to 18 MHz, more preferably in a frequency range of 1 MHz to 15 MHz and most preferably in a frequency range of 3 MHz to 10 MHz. If the wave is an electromagnetical wave, it is preferably light, in particular monochromatic light. The measuring device then preferably comprises a laser. Alternatively, the measuring device could also be adapted to measure an electrical conductance in the heart or the blood vessel to determine the respective inner volume. To this end, the measuring device can apply a conductance or an admittance technique.

In order to optimally implement the Frank-Starling law, the controller is preferably configured to determine an estimate for the end-diastolic volume (EDV) of the heart, in order to regulate the power (or pump speed) of the blood pump. The controller is particularly configured to regulate the power of the blood pump based on the following linear function:

$$PW_{des}(t)=(EDV(t)-EDV_0) \cdot k_{prsw},$$

in which $PW_{des}(t)$ denotes the desired pump work per heartbeat at a certain time t and $EDV(t)$ an estimate of the end-diastolic volume of the heart determined based on the measured physical parameter, and in which the two parameters $EDV_0$ and $k_{prsw}$ denote the end-diastolic volume at which the desired pump work is zero and the gain of the pump work relative to the estimated $EDV(t)$, respectively.

By regulating the power according to a linear function with respect to $EDV(t)$, the concept of the preload recruitable stroke work (PRSW) as a linear, afterload-independent model of the Frank-Starling law is implemented, as presented in: Glower D D, Spratt J A, Snow N D, et al. Linearity of the frank-starling relationship in the intact heart: the concept of preload recruitable stroke work. Circ 1985; 71:994-1009. This concept has proven to be a very realistic model for the physiological regulation of the cardiac function.

A particularly physiological regulation of the blood pump is achieved, if $k_{prsw}$ is in the range of 0.003 J/ml to 0.02 J/ml, and in particular in the range of 0.006 J/ml to 0.012 J/ml.

In order to regulate the power of the blood pump close to the model specified by the Frank-Starling law, $EDV_0$ is preferably in the range of 10 ml to 150 ml, in particular in the range of 25 ml to 90 ml.

Advantageously, the controller is configured to also determine an estimate for the heart rate of the patient based on the measured at least one physical parameter. The heart rate can be used particularly for calculating the power of the blood pump after having determined the desired pump work per heartbeat. Of course, the heart rate can also be used for other purposes, such as for detecting a sudden arrhythmia, tachycardia or a ventricular fibrillation, in order to regulate the power of the blood pump according to a special scheme being specifically provided for such a case.

The controller is advantageously configured to detect an asystolic cardiac motion, preferably by determining the pulsatility of the inner volume of the heart, and to regulate the power of the blood pump according to a special mode, if an asystolic cardiac motion has been detected. If the heart is assumed to be asystolic or to be in a state of arrhythmia, tachycardia or fibrillation, the regulation of the power of the blood pump is preferably carried out according to a special mode particularly suited for this case. Advantageously, the apparatus is configured to automatically switch into a special mode, when detecting such an abnormal functional state of the heart. Additionally or alternatively, the biomedical apparatus can comprise a device for allowing the patient or the medical personnel to manually switch the apparatus into the special mode.

Furthermore, a method for operating a biomedical apparatus for pumping blood of a human or an animal patient through a secondary intra- or extracorporeal blood circuit is provided, wherein the biomedical apparatus is preferably constructed as stated above and comprises a blood pump for pumping blood, an inlet duct connected to the blood pump, for being inserted into a patient's circulatory system, in order to guide blood of the patient to the blood pump, and an outlet duct connected to the blood pump, for being inserted into the patient's circulatory system, in order to guide blood from the blood pump back to the patient's circulatory system. The method comprises at least the following steps:

measuring at least one physical parameter of the heart or of a blood vessel of the patient, and regulating the power of the blood pump based on the measured physical parameter.

The physical parameter is measured by means of a measuring device arranged inside the heart or the blood vessel, and an estimate for an inner volume of the heart or of the blood vessel is determined based on the physical parameter. The power of the blood pump is regulated depending on this estimate.

Preferably, the physical parameter is measured by measuring at least one distance between the measuring device and a ventricular wall of the heart or between the measuring device and a vascular wall of the blood vessel, in particular by means of an ultrasound measurement and advantageously in a plurality of differing directions.

BRIEF DESCRIPTION OF THE DRAWINGS

Preferred embodiments of the invention are described in the following with reference to the drawings, which only serve for illustration purposes, but have no limiting effects. In the drawings it is shown.

DESCRIPTION OF PREFERRED EMBODIMENTS

Figure 1:
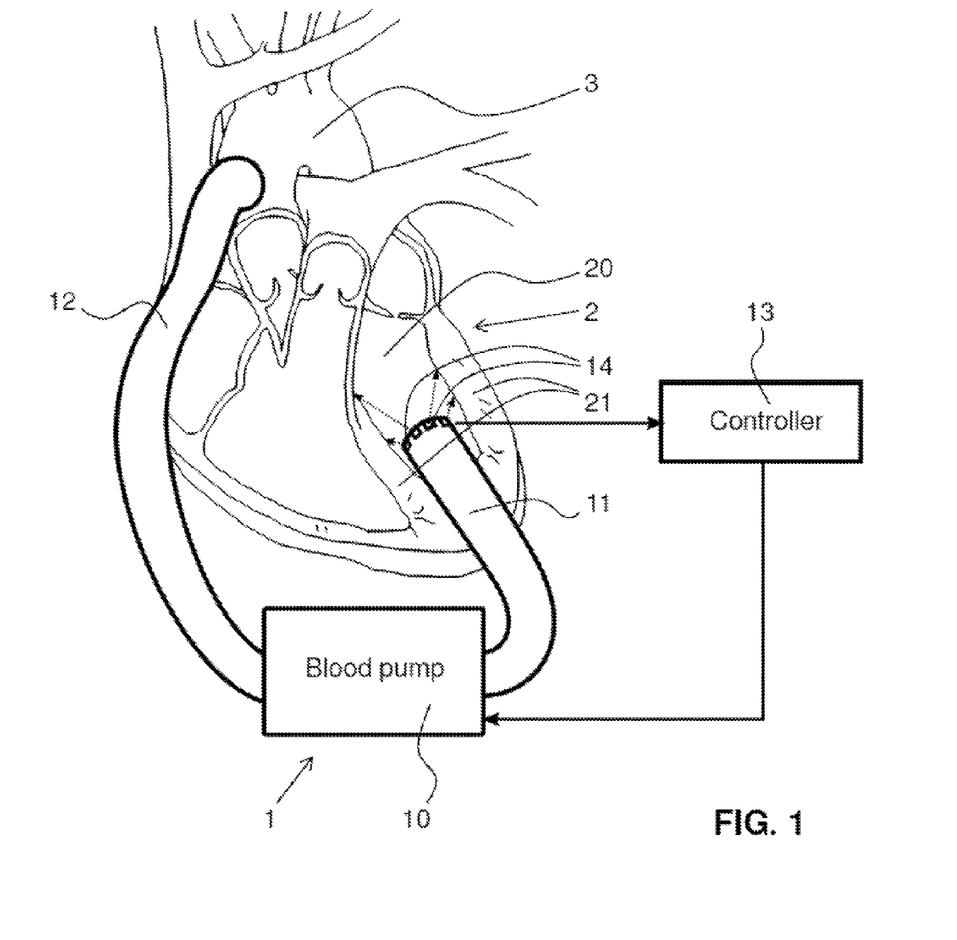
FIG. 1 a schematic view of a Ventricular Assist Device (VAD) according to the invention, implanted in the heart of a patient.

In FIG. 1, an inventive embodiment of a biomedical apparatus for pumping blood of a human or an animal patient through a secondary intra- or extracorporeal blood circuit is shown. The apparatus of this embodiment is a Ventricular Assist Device (VAD) 1 used to partially or completely replace the function of a heart 2 of a patient with heart failure.

The VAD 1 comprises a blood pump 10, which can be a pneumatically or electrically actuated pulsatile volumetric pump, or an axial or centrifugal turbodynamic pump with classical contact bearings, with a magnetically levitated rotor or with a blood-immersed bearing. A large variety of pumps of these kinds and suited for being used in a VAD are known to the person skilled in the art.

Connected to the blood pump 10 is an inlet duct or, here, an inlet cannula 11, which has a free end being inserted into the left ventricle 20 in the region of the apex of the heart 2. The inlet cannula 11 serves to guide blood from the inside of the left ventricle 20 to the blood pump 10. Due to the pumping action of the blood pump 10 the blood is drawn through an inlet opening located at the free end of the inlet cannula 11 into the inlet cannula 11 and to the blood pump 10.

In direction of the blood stream, an outlet duct or, here, an outlet cannula 12 is connected to the blood pump 10 on the opposite side relative to the inlet cannula 11. The outlet cannula 12 serves to guide the blood from the blood pump 10 back to the patient's circulatory system. To this end, the outlet cannula 12 is inserted into the aorta 3 of the patient.

The inlet cannula 11, the blood pump 10 and the outlet cannula 12 together constitute a secondary blood circuit, which is preferably located completely inside the body of the patient. The blood streaming through this secondary blood circuit originates from the left ventricle 20 and streams into the aorta 3. Within the secondary blood circuit, the blood is pumped by the blood pump 10 in the direction towards the aorta 3. Thus, the blood pump 10 supports the function of the (failed) heart 2.

The output power by which the blood is pumped into the outlet cannula 12 by the blood pump 10 is regulated by a controller 13 which is able to communicate with a measuring device 14 attached to the inlet cannula 11 and the blood pump 10. The controller 13 can particularly be represented by an integral circuit and preferably comprises at least one data storage module. The regulation of the power of the blood pump 10 by the controller 13 is based on the determination of an estimate for the inner volume of the left ventricle 20 at end-diastole. In order to obtain an estimate of the inner ventricular volume for regulating the power of the blood pump 10, physical parameters in the form of a plurality of distances between the free end of the inlet cannula 11 and the inner surface of the ventricular wall 21 are measured in differing directions. These measurements are carried out by a plurality of ultrasound transceivers 14 being arranged on the free end of the inlet cannula 11.

The ultrasound transceivers 14 are adapted both to send out ultrasound waves and to receive ultrasound waves. In order to measure a distance between an ultrasound transceiver 14 and the inner surface of the ventricular wall 21, the ultrasound transceiver 14 sends out an ultrasound wave (see arrows in FIG. 1), which is reflected on the tissue boundary at the surface of the ventricular wall 21. The reflected ultrasound wave is received by the same (and optionally also by other) ultrasound transceiver(s) 14. The time period measured for the ultrasound wave to travel from the transceiver 14 to the ventricular wall 21 and back to the transceiver 14 is used to calculate the distance between the transceiver 14 and the inner surface of the ventricular wall 21. This calculation is usually carried out in the controller 13. From the different measurements of the distances between the inlet cannula 11 and the ventricular wall 21 in differing directions, an estimate for the actual left ventricular volume LVV at the time of the measurement is calculated by the controller 13.

Figure 2:
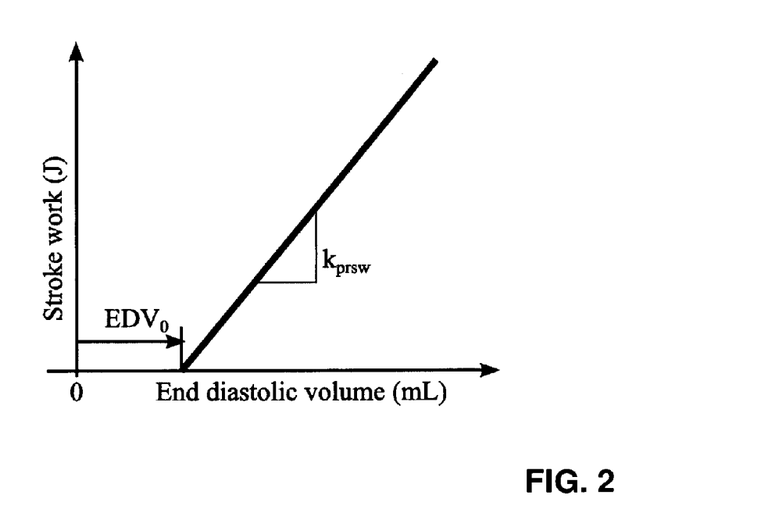
FIG. 2 a graph illustrating the preload recruitable stroke work (PRSW): stroke work as a function of end diastolic volume.

The estimate for the left ventricular volume is used to determine an estimate for the end-diastolic volume (EDV) of the heart 2. Based on the estimate for the end-diastolic volume, the desired stroke work ($PW_{des}$) of the blood pump 10 per heartbeat is calculated by the controller 13 according to the concept of preload recruitable stroke work (PRSW), as illustrated in FIG. 2. Thus, the regulation of the power of the blood pump 10 by means of the controller 13 is based on the theory of venous return (Guyton A C, Hall J E. Textbook of Medical Physiology, 12th Edition. Saunders W B Co, 2010.) and the Frank-Starling law of the heart. FIG. 2 shows a graphical interpretation of the PRSW. This model states that the stroke work of the left ventricle increases linearly with the end-diastolic volume EDV. The PRSW has been evaluated in a group of 60 patients with an average age of 59.4±8.7 years in: Takeuchi M, Odake M, Takaoka H, Hayashi Y, Yokoyama M. Comparison between preload recruitable stroke work and the end-systolic pressure-volume relationship in man. Eur Heart J 1992; 13:80-84. In baseline, the PRSW curves of these patients are described by the slope $k_{prsw}$=0.00898±0.00299 J/ml and the x-axis intercept $EDV_0$=38.0±27.0 ml. An increased contractility of the LV increases the slope of the PRSW. Since the output (stroke work) of the heart is proportional to the input (end-diastolic volume EDV), the PRSW can be viewed as a proportional controller of the heart. Hence, the controller 13 imitates the PRSW by proportionally adjusting the pump power based on the determined EDV.

Figure 3:
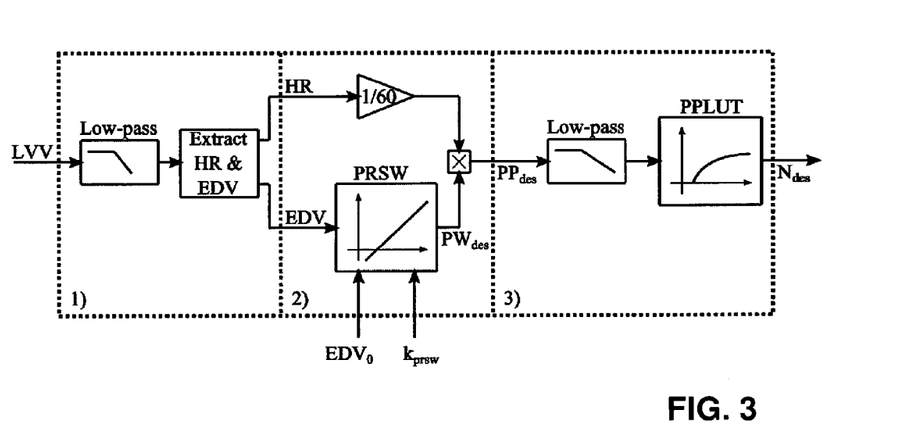
FIG. 3 a schematic representation of the main control structure of the controller of a VAD according to the invention.

As shown in FIG. 3, in which the main control structure of the controller 13 is shown, the input of the main control structure of the controller 13 is the estimate for the actual left ventricular volume LVV; the output is the desired pump speed $N_{des}$, which in turn is transmitted to a pump speed controller of the blood pump 10. The control structure according to the present embodiment is implemented as a discrete-time system with a sampling frequency of 100 Hz. The main control structure of the controller 13 can be subdivided into three stages 1)-3). In the first stage 1), signal processing algorithms are used to determine the end-diastolic volume EDV and the heart rate HR. In the second stage 2), the determined end-diastolic volume EDV and heart rate HR are used to calculate a desired pump power $PP_{des}$. This part of the control structure imitates the PRSW. The third stage 3) of the algorithm uses the desired power to compute a desired pump speed that approximately achieves the desired power.

Figure 4A:
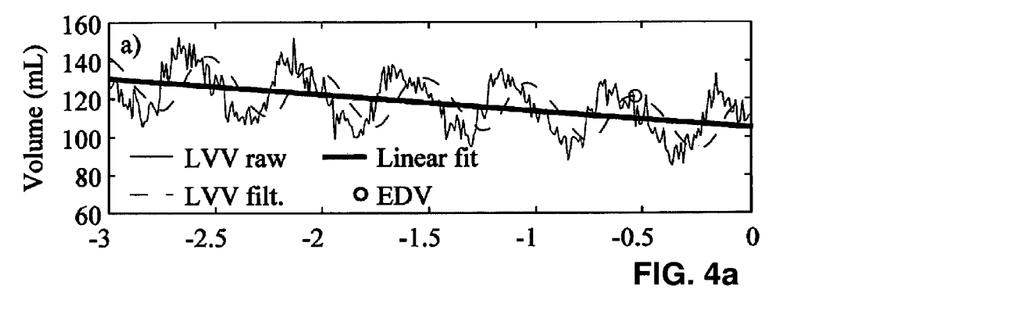
FIG. 4a a graph illustrating the raw and the filtered signals of the left ventricular volume (LVV) as well as a linear fit to the filtered LVV signal.
Figure 4B:
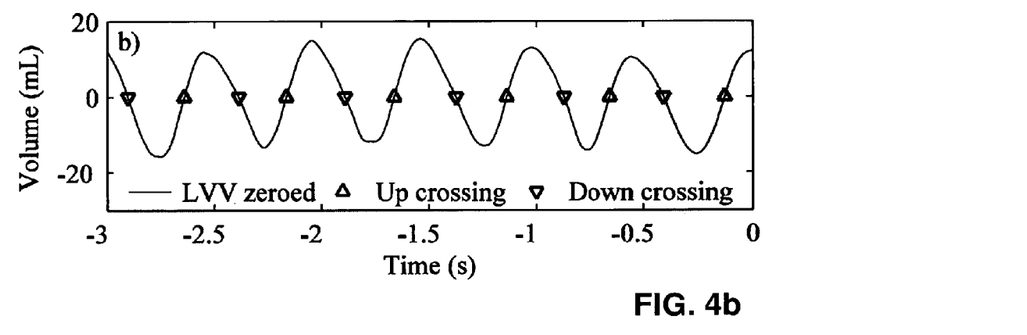
FIG. 4b a graph illustrating the zeroed LVV signal.

The first stage 1) of the control structure takes the left ventricular volume LVV signal as an input and computes the end-diastolic volume EDV and the heart rate HR. FIGS. 4a and 4b illustrate the signal processing procedure carried out in this stage 1) for a simulated left ventricular volume LVV signal with subsequently added zero-mean white noise ($\sigma=5$ ml) and a sampling time of 10 ms. First, the left ventricular volume signal (LVV raw) is low-pass filtered using a second-order IIR filter. The resulting signal is denoted with LVV filt. in FIG. 4a. Then, using a sliding window, the last 3 s of the LVV signal are acquired at every time step. FIG. 4a shows the 3 s window with the raw and the filtered LVV signals. The instantaneous HR and EDV signals are calculated from this window as follows: First, an affine function is fitted to the filtered LVV signal using the least-squares method (linear fit in FIG. 4a). This affine function represents the offset and a linear trend of the LVV signal. Second, this affine function is subtracted from the filtered signal, which yields a zero-mean sine-like signal as shown in FIG. 4b. Third, all zero crossings and the direction of their crossing are detected. Fourth, the time intervals between all subsequent downward crossings and all subsequent upward crossings are calculated. Fifth, the heart rate HR is calculated by dividing 60 by the median of all previously calculated time intervals. And sixth, the estimate for the end-diastolic volume EDV is calculated by taking the maximum value of the filtered LVV signal between the last downward crossing and the last preceding upward crossing as indicated in FIG. 4a. All six steps of the algorithm are repeated at every time-step of the controller 13.

If the heart is asystolic, the HR and EDV detection described above is not valid, since the LVV signal does not have a sine-like shape. Such a case is detected by the signal processing procedure, and an alternative algorithm is then used by the controller 13 for the HR and EDV detection. The detection of an asystolic heart is based on the pulsatility of the LVV signal. This implementation allows the controller 13 to be used in patients without a regular or an undetectable heart rate.

The second stage 2) of the main control structure of the controller 13, as shown in FIG. 3, consists of one part describing the preload recruitable stroke work PRSW and an additional part to include the heart rate HR. The PRSW is implemented as a linear function of the EDV:

$$PW_{des}(t)=(EDV(t)-EDV_0) \cdot k_{prsw},$$

where $EDV_0$ is the x-axis intercept and $k_{prsw}$ is the gain of the stroke work with respect to the EDV according to the PRSW (see FIG. 2). This function calculates the desired pump work per heartbeat $PW_{des}(t)$ at a time t. The two parameters $EDV_0$ and $k_{prsw}$ can be adapted by the physician, by trained medical personnel or by the patient. The desired pump power $PP_{des}$ is calculated by:

$$PP_{des}(t)=PW_{des}(t) \cdot HR(t)/60.$$

Figure 5:
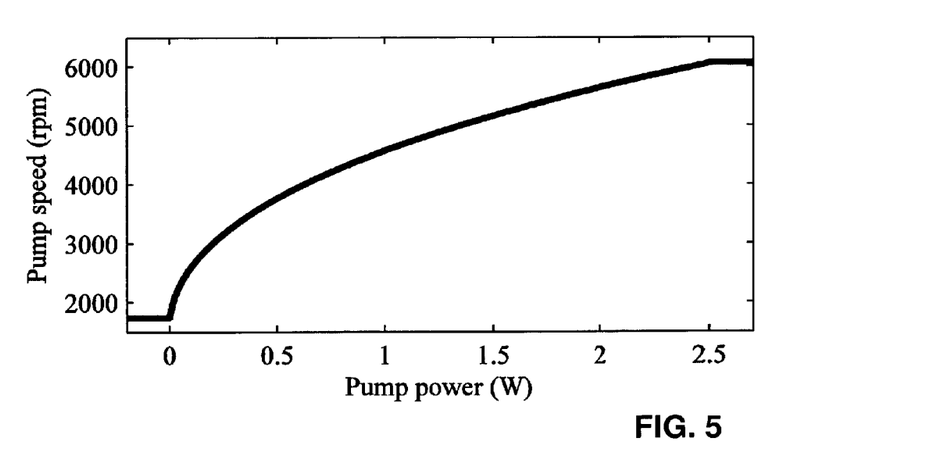
FIG. 5 a graph illustrating the pump-power lookup-table (PPLUT): pump speed as a function of pump power.

The third stage 3) of the main control algorithm, as shown in FIG. 3, consists of a low-pass filter and a lookup-table. The low-pass element is a first-order IIR filter with a cut-off frequency of 1 rad/s. The pump-power lookup-table (PPLUT) is a mapping between the hydraulic pump power and the pump speed. The actual power delivered by the pump is not only a function of the pump speed, but also the resistance against the pump flow and the fluid viscosity, but for the implementation in the controller 13, these dependencies are neglected and the pump speed directly mapped to a pump power. FIG. 5 shows the pump-power lookup-table PPLUT implemented in the controller 13.

The presented controller 13 according to the embodiment as illustrated FIGS. 1-5 adapts the cardiac output very similar to the physiological circulation, while effectively preventing overpumping and underpumping. The controller 13 shows a high sensitivity towards preload changes and a low sensitivity to afterload changes. The pump speed adaptation with regard to the blood pump 10 is fast and keeps the left ventricular volume in a safe range. The main control structure of the controller 13 is very simple and only two parameters need to be adapted, namely $k_{prsw}$ and $EDV_0$. The adaptation of these two parameters could be made by the physician, trained medical personnel, or the patient in order to find a comfortable level of perfusion. As long as $k_{prsw}$ is kept between certain limits, the controller 13 retains its safe operation.

The invention is of course not limited to the preceding presented embodiment and a plurality of modifications is possible. For example, the controller 13 with the main control structure as presented above could also be used for controlling the output power of a blood pump in an extracorporeal membrane oxygenation (ECMO) apparatus, a heart-lung machine or a dialysis apparatus. The measurement of the distances does not necessarily be carried out by means of ultrasound transceivers. Optical measuring devices, such as a laser, or an electrical conductance measuring device, such as an admittance or conductance catheter, could also be used for this purpose. Instead of determining an estimate for the inner volume of the left ventricle, it would also be conceivable to determine an estimate for the inner volume of the right ventricle, the left or the right atrium or of a certain section of a blood vessel. The inlet and the outlet cannulas do not necessarily be inserted into in the left ventricle 20 and the aorta 3, respectively, but could be inserted at any other location of the circulatory system, depending on the concrete purpose of the biomedical apparatus. It would also be conceivable to construct the measuring device as a separate part with respect to the inlet cannula and to even arrange the measuring device at a different location in the circulatory system than the inlet cannula. For example, the inlet cannula could be inserted into the aorta 3 or into any other blood vessel and the measuring device could be located in the left ventricle. It can be imagined that the controller 13 is used as the low-level controller in a hierarchical control system. A high-level control system could then influence the $k_{prsw}$ of the controller and influence the controller gain, while maintaining the safe operation of the controller. Such a high level controller could be based on an additional measurement, e.g. a measurement of the patient movement (acceleration sensor) or the blood oxygen concentration. A plurality of further modifications is possible.

| REFERENCE NUMERALS | | | |
|---|---|---|---|
| 1 | Ventricular Assist Device (VAD) | 14 | Ultrasound transceivers |
| | | 2 | Heart |
| 10 | Blood pump | 20 | Left ventricle |
| 11 | Inlet cannula | 21 | Ventricular wall |
| 12 | Outlet cannula | 3 | Aorta |
| 13 | Controller | | |

The invention claimed is:

1. A biomedical apparatus for pumping blood of a human or an animal patient through a secondary intra- or extracorporeal blood circuit, comprising
a blood pump for pumping blood,
an inlet duct connected to the blood pump, for being inserted into a patient's circulatory system, in order to guide blood of the patient to the blood pump,
an outlet duct connected to the blood pump, for being inserted into the patient's circulatory system, in order to guide blood from the blood pump back to the patient's circulatory system,
a measuring device for measuring at least one physical parameter of the heart or of a blood vessel of the patient, the measuring device being adapted to be arranged inside the heart or the blood vessel and being adapted to send out an electromagnetic or a mechanical wave, and
a controller being configured to determine an estimate for an end-diastolic inner volume of the heart based on the measured physical parameter and being configured to regulate the power of the blood pump based on the following linear function:

$$PW_{des}(t)=(EDV(t)-EDV_0)\cdot k_{prsw},$$

in which $PW_{des}(t)$ denotes the desired pump work per heartbeat at a certain time t and EDV(t) the estimate for the end-diastolic volume of the heart determined based on the measured physical parameter, and in which the two parameters $EDV_0$ and $k_{prsw}$ denote the end-diastolic volume at which the desired pump work is zero and the gain of the pump work relative to the estimated EDV(t), respectively.

2. The biomedical apparatus as claimed in claim 1, wherein the measuring device is arranged on the inlet duct.

3. The biomedical apparatus as claimed in claim 1, wherein the biomedical apparatus is a Ventricular Assist Device (VAD), a heart-lung machine or an extracorporeal membrane oxygenation (ECMO) apparatus.

4. The biomedical apparatus as claimed in claim 1, wherein the physical parameter is a distance between the measuring device and a ventricular wall of the heart or between the measuring device and a vascular wall of the blood vessel.

5. The biomedical apparatus as claimed in claim 4, wherein the measuring device is adapted for measuring a plurality of distances between the measuring device and the ventricular wall or between the measuring device and the vascular wall in differing directions.

6. The biomedical apparatus as claimed in claim 1, wherein the measuring device is an ultrasound measuring device suited for carrying out ultrasound measurements.

7. The biomedical apparatus as claimed in claim 1, wherein $k_{prsw}$ is in the range of 0.003 J/ml to 0.02 J/ml.

8. The biomedical apparatus as claimed in claim 7, wherein $k_{prsw}$ is in the range of 0.006 J/ml to 0.012 J/ml.

9. The biomedical apparatus as claimed in claim 1, wherein $EDV_0$ is in the range of 10 ml to 150 ml.

10. The biomedical apparatus as claimed in claim 9, wherein $EDV_0$ is in the range of 25 ml to 90 ml.

11. The biomedical apparatus as claimed in claim 1, wherein the controller is configured to determine an estimate for the heart rate of the patient based on the measured physical parameter.

12. The biomedical apparatus as claimed in claim 1, wherein the controller is configured to detect an asystolic cardiac motion and to regulate the power of the blood pump according to a special mode, if an asystolic cardiac motion has been detected.

13. A method for operating a biomedical apparatus for pumping blood of a human or an animal patient through a secondary intra- or extracorporeal blood circuit, wherein the biomedical apparatus comprises a blood pump for pumping blood, an inlet duct connected to the blood pump, for being inserted into a patient's circulatory system, in order to guide blood of the patient to the blood pump, and an outlet duct connected to the blood pump, for being inserted into the patient's circulatory system, in order to guide blood from the blood pump back to the patient's circulatory system, and wherein the method comprises at least the following steps:
measuring at least one physical parameter of the heart or of a blood vessel of the patient by means of electromagnetic or mechanical waves sent out by a measuring device arranged inside the heart or the blood vessel,
determining an estimate for an end-diastolic inner volume of the heart based on the measured physical parameter, and
regulating the power of the blood pump based on the following linear function:

$$PW_{des}(t)=(EDV(t)-EDV_0)\cdot k_{prsw},$$

in which $PW_{des}(t)$ denotes the desired pump work per heartbeat at a certain time t and EDV(t) the estimate for the end-diastolic volume of the heart determined based on the measured physical parameter, and in which the two parameters $EDV_0$ and $k_{prsw}$ denote the end-diastolic volume at which the desired pump work is zero and the gain of the pump work relative to the estimated EDV(t), respectively.

14. The method as claimed in claim 13, wherein the physical parameter is measured by measuring at least one distance between the measuring device and a ventricular wall of the heart or between the measuring device and a vascular wall of the blood vessel.

* * * * *